(12) United States Patent
Lin

(10) Patent No.: US 6,825,119 B1
(45) Date of Patent: Nov. 30, 2004

(54) METHOD OF PIPING DEFECT DETECTION

(75) Inventor: Long-Hui Lin, Hsin-Chu Hsien (TW)

(73) Assignee: Powerchip Semiconductor Corp., Hsin-Chu (TW)

( * ) Notice: Subject to any disclaimer, the term of this patent is extended or adjusted under 35 U.S.C. 154(b) by 0 days.

(21) Appl. No.: 10/707,952

(22) Filed: Jan. 28, 2004

(30) Foreign Application Priority Data

Aug. 28, 2003 (TW) .......................... 92123827 A

(51) Int. Cl.[7] .......................................... H01L 21/461
(52) U.S. Cl. ......................................................... 438/692
(58) Field of Search .................. 438/692; 714/718; 349/27; 250/310; 382/147

(56) References Cited

U.S. PATENT DOCUMENTS 5,896,395 A * 4/1999 Lee ............................ 714/718
5,958,794 A * 9/1999 Bruxvoort et al. ........... 438/692
6,317,514 B1 * 11/2001 Reinhorn et al. ............ 382/147
6,424,388 B1 * 7/2002 Colgan et al. ................. 349/27
6,777,676 B1 * 8/2004 Wang et al. .................. 250/310

* cited by examiner

*Primary Examiner*—John F. Niebling
*Assistant Examiner*—Andre C. Stevenson
(74) *Attorney, Agent, or Firm*—Winston Hsu

(57) ABSTRACT

A method of piping defect detection is disclosed. First, a sample is provided. The sample has a silicon substrate, a plurality of electric devices disposed on the silicon substrate surface, a dielectric layer covering the electric devices and the substrate, and a polysilicon layer positioned on the dielectric layer, which is electrically connected to the electric devices through contact holes in the dielectric layer. A chemical mechanical polish process is performed to remove the polysilicon layer on the dielectric layer and parts of the dielectric layer. A wet etching process is then performed to delayer the dielectric layer. After that, the sample is inspected under an ultraviolet light irradiation for detecting the piping defects in the dielectric layer of the sample.

17 Claims, 4 Drawing Sheets

METHOD OF PIPING DEFECT DETECTION

BACKGROUND OF INVENTION

1. Field of the Invention

The present invention relates to a method of piping defect detection, and more particularly, to a fast and sensitive method of piping defect detection.

2. Description of the Prior Art

In the semiconductor fabricating process, after electric devices, such as MOS transistors, are formed in a substrate, a dielectric layer, which is a so-called inter layer dielectric layer, is typically formed thereon for isolating and protecting the electric devices beneath. Normally, a plurality of contact holes are disposed in the inter layer dielectric layer for filling a conductive layer which is used to form a contact plug in each of the contact holes. Thus, the electric devices can electrically connect with other external electric devices, such as a conductive wire, through the contact plugs. Hence, data signals can be transferred to the electric devices, such as a source or drain of a transistor, through the conductive wire and the contact plug to control the operation of each electric device.

A DRAM wafer is illustrated in the following to describe a fabricating method of the contact plug in the prior art. Please refer to FIG. 1 and FIG. 2, which are schematic diagrams of a method of forming an electric connection through contact plugs. As shown in FIG. 1, a wafer 10 comprises a substrate 12, and transistors 14, 16, 18, and 20 disposed on the surface of the substrate 12. The transistor 14 uses the same silicon layer as its gate with the transistor 18 and the same doped region as its source with the transistor 16. In the same manner, the transistor 20 shares a polysilicon layer with the transistor 16 and a source with transistor 18. As shown in FIG. 2, a dielectric layer 22, such as a borophospho-tetra-ehtyl-ortho silicate (BPTEOS) layer, is deposited on the wafer 10. Then a photo-etching process is used to form a plurality of contact holes in the dielectric layer 22. After that, a conductive layer (not shown), such as a polysilicon layer, is deposited on the dielectric layer 22 to fill the contact holes for forming contact plugs 26, 28, 30, 32, 34, and 36.

As the process size shrinks and the integration of device increases, when the dielectric layer 22 is deposited, a plurality of voids 24 with piping shapes are easily formed among gates due to the low filling ability of the dielectric layer 22. Thus, some contact holes connect with each other. Although a rapid heat treatment is often used to perform a reflow process for reducing the voids 24, the presence of voids 24 can not be prevented in most cases. Therefore, in the following process of contact plug formation, some contact plugs will connect with or short each other, such as the contact plugs 34 and 36 shown in FIG. 2, that cause the transistors 14, 16, 18, and 20 to not operate properly. It is a so-called piping defect.

For clarity, the wafer 10 is illustrated as a detected sample to describe the conventional method of piping defect detection. Please refer to FIG. 3, which is a schematic diagram of the method of piping defect detection in the prior art. The piping defects often appear in a distance under the surface of the dielectric layer 22. Thus, a proper pretreatment is required for the sample before performing the defect inspection. As shown in FIG. 3, in the conventional method of piping defect detection, after sampling 50, a chemical mechanic polish (CMP) process 60 is performed to remove layers on the dielectric layer, such as a polysilicon layer for forming the contact plug. Then, a wet etching process 70 is used to remove parts of the dielectric layer 22. After that, a defect inspection 80 is performed with a scanning electron microscope (SEM). According to the result of the defect inspection 80, a failure bit map (FBM) can be made to analyze the root cause of piping defects in advance for reducing the generation of voids 24 by adjusting the fabricating process parameters properly.

However, the defect inspection 80, which is the last step of the piping defect detection in the prior art, must be manually inspected by engineers, which requires a lot of time and effort. For example, it normally takes more than 12 hours to inspect a batch of 50 samples. When any problem appears in the deposition of the dielectric layer 22, it will be detected or found in the wafer test performed two months latter. It is obvious that engineers have to spend more time in the process parameter tuning to find a proper process margin of the deposition process. In addition, since the piping defects are very small, normally with a size below 0.1 $\mu$m for a DRAM of 0.13 $\mu$m process, it is too hard for engineers to examine the wafer in a large scale inspection. Moreover, engineers often make careless mistakes while examining the wafer and do not notice the presence of the piping defects. This leads to serious problems in the following root cause analysis process. Thus, process parameters cannot be adjusted properly and efficiently and the reliability of the products is thereby deteriorated.

Along with the promotion of the semiconductor fabricating process and the scaling-up due to economic reasons, the diameter of semiconductor wafers is increasing from 8 inches to 12 inches, and the line width is also shrinking from 0.18 $\mu$m to 0.13 $\mu$m, and even to 0.1 $\mu$m. During the time of great process updates, a high level of experience and testing is required to confirm the margins of each process parameter so that the reliability of products can be maintained during mass production. It is obvious that the conventional technology cannot meet the requirement. Conventional technology always requires a lot of time and cost, but the correct process margins of parameters are still not obtained. Thus, a fast and sensitive method of defect detection is required to solve aforementioned problems.

SUMMARY OF INVENTION

It is therefore a primary objective of the claimed invention to provide a fast and sensitive method of piping defect detection to solve the aforementioned problems in the prior art.

In a preferred embodiment of the claimed invention, a sample is first proved. The sample comprises a silicon substrate, a plurality of electric devices disposed thereon, a dielectric layer covering the plurality of electric devices and the silicon substrate, and a polysilicon layer formed on the dielectric layer electrically connected to the electric devices through contact holes in the dielectric layer. A chemical mechanic polishing process is performed to remove the polysilicon layer and parts of the dielectric layer of the sample. Then, a wet etching process is performed to remove parts of the dielectric layer. After that, the sample is inspected under an ultraviolet light irradiation for detecting the piping defects in the dielectric layer of the sample.

It is an advantage of the claimed invention that since the defects can be detected under the UV light irradiation according to the brightness contrast between the polysilicon layer and the silicon oxide layer after a CMP process and a wet etching process are used to pretreat the sample, a real-time automatic defect classification (ADC) tool can be applied to detect the online samples. Thus, the yield and reliability of products can be improved effectively.

These and other objectives of the claimed invention will no doubt become obvious to those of ordinary skill in the art after reading the following detailed description of the preferred embodiment which is illustrated in the various figures and drawings.

DETAILED DESCRIPTION

Figure 1:
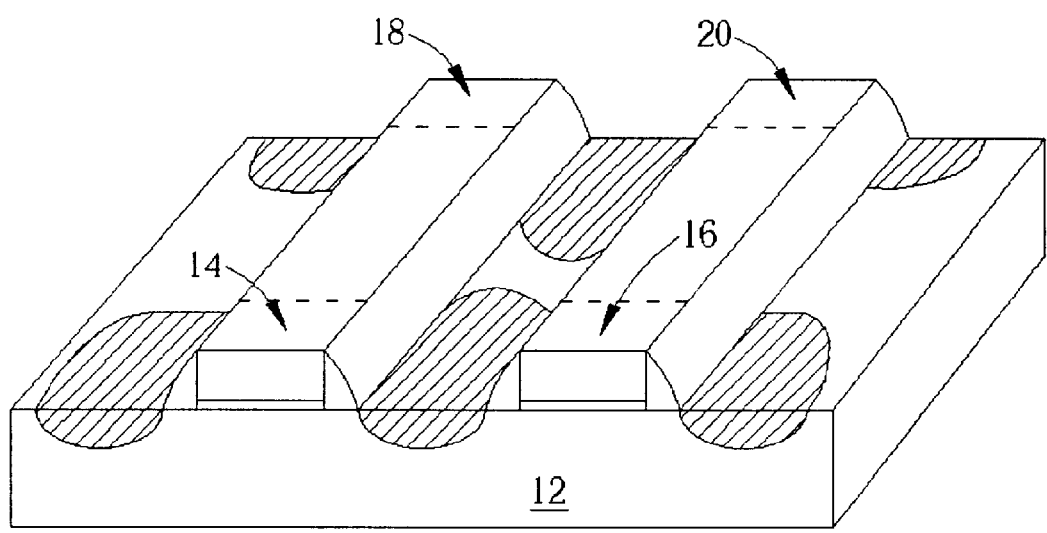
FIG. 1 and FIG. 2 are schematic diagrams of a method of forming an electrical connection via contact holes.
Figure 2:
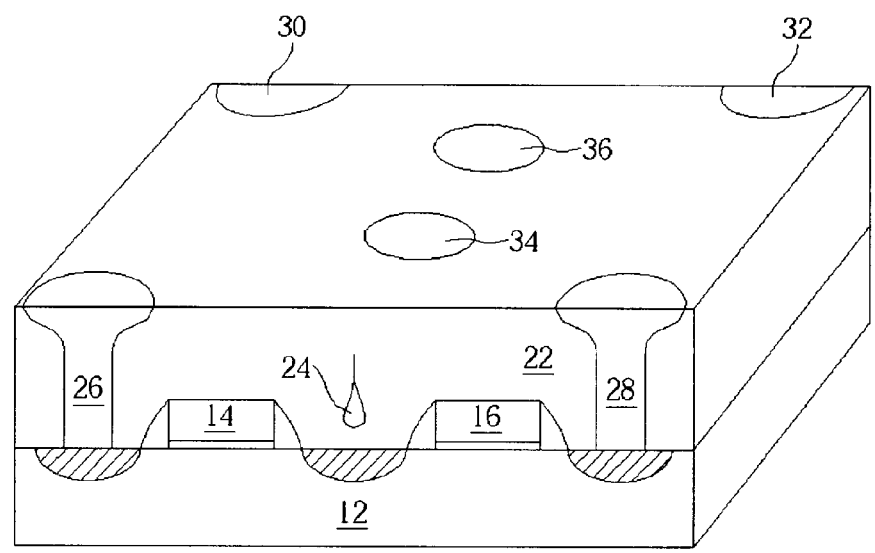
Figure 3:
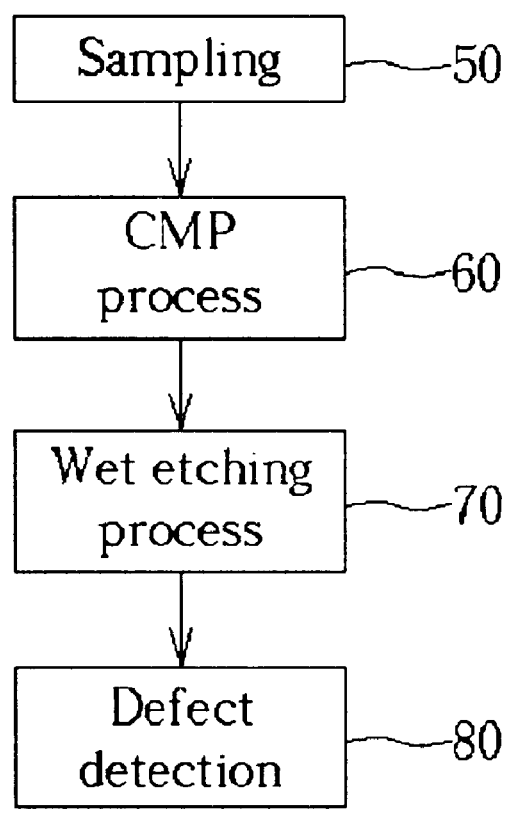
FIG. 3 is a schematic diagram of a conventional method of piping defect detection.
Figure 4:
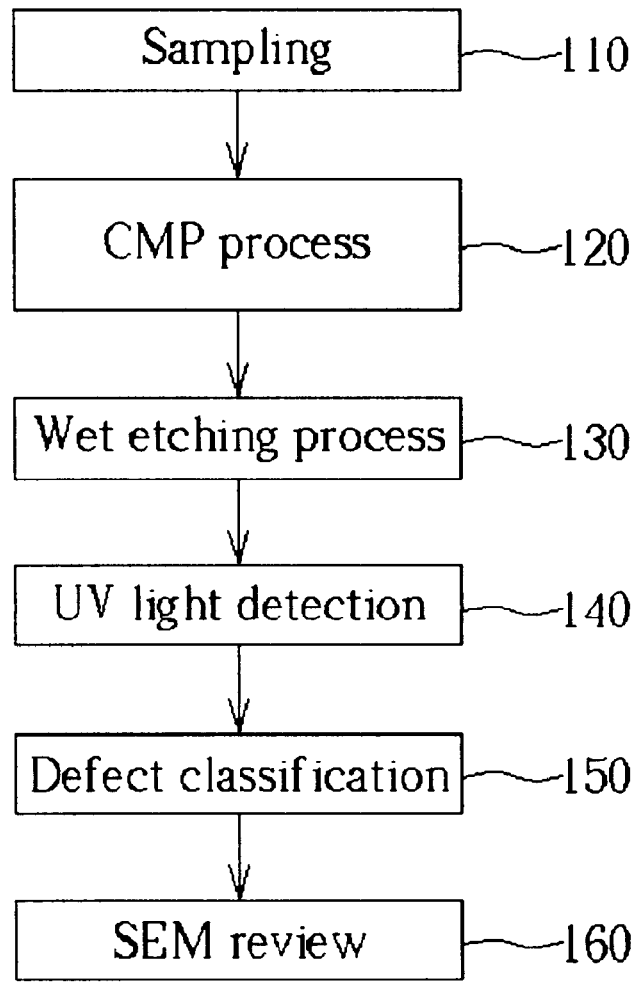
FIG. 4 is a schematic diagram of a method of piping defect detection in the present invention.

For clearly explaining the difference between a method of defect detection of the present invention and that of the prior art, the same inspecting sample, which is the wafer 10, is used in the following description to describe the method of defect detection of the present invention. Please refer to FIG. 4, which is a schematic diagram of a method of defect detection according to a preferred embodiment of the present invention. As shown in FIG. 4, after sampling 110, a chemical mechanic polishing process (CMP) 120 and a wet etching process 130 are used to pretreat the wafer 10. It is noted that after an interface between the conductive layer and the dielectric layer 22 is exposed in the CMP process 120, the CMP process 120 in the preferred embodiment of the present invention continues an over etching to remove a certain thickness of the dielectric layer 22 until each contact plug does not overlap with the gates. Since the width of each void 24 is generally increasing from the top to the bottom of the void 24, the pretreatment can significantly increase the width of the opening of each void 24 in the dielectric layer 22 so the followed inspection can be performed more easily. In the preferred embedment of the present invention, the thickness of the over etching is about 300 to 1000 angstroms and can be further adjusted according to the thickness of the dielectric layer. Then, a proper wet etching process 130 can be followed to remove the parts of the dielectric layer by a selective etching to reduce the thickness of the dielectric layer 22 for the next defect inspection process.

After that, an ultra-violent (UV) light inspection 140 is performed. In the UV light inspection 140, the wafer 10 is inspected in a proper amplifying scale under an UV light, such as a wide band UV light or a narrow band UV light. Since there is a great difference in material between the dielectric layer 22 and the polysilicon layer, which is used to form the contact plug, if there is any defect existing, an apparent brightness difference can be found in the inspected image in the areas surrounding the defect. For example, the dielectric layer 22, which is composed of a BPTEOS layer, has a black image with a low brightness under the UV light irradiation, but the contact plug, which is composed of a polysilicon layer, has a white image with a high brightness. If there is any defect existing in the dielectric layer 22, the location of the defect becomes relative transparent and has a higher brightness in comparison with the image of surrounding regions. Thus, a shape, size, and position of the defect can be detected easily. It is noted that although a UV light is used for detecting piping defects in the preferred embodiment aforementioned, the light source of the present invention is not limited to this. Some other types of light sources can be used to perform the piping defect detection if distinguishable images of the dielectric layer 22 and the polysilicon layer can be formed, such as forming an opaque image for the polysilicon layer and a transparent image of the dielectric layer 22.

After the shape, size, and location of defects in the wafer 10 are detected, an automatic defect classification (ADC) tools can be used to perform an automatic defect classification 150 for the sample. By using a pre-built database, the piping defects and other defects can be separated automatically. In addition, a manual SEM review 160 can be further performed by engineers to analyze the root cause of the defects. Since the approximate location of each defects are already known, the accuracy and efficiency of the SEM review 160 can be improved greatly. Therefore, process parameters, such as the velocity and the temperature of the depositing process, the temperature and the duration of a rapid heating process, and a line width of the gate, can be adjusted correspondingly according to the result of the root cause analysis to reduce the presence of the defects and improve the yield and the reliability of products.

In contrast to the prior art, the present invention detects defects according to a brightness difference under a UV light irradiation instead of the manual inspection with the scanning electron microscope in the prior art. Thus, the efficiency and the accuracy of the defect detection can be greatly improved. In addition, a requirement of an online test can be met to adjust process parameters in a relatively short time for improving the throughput and the reliability of products.

Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A method of piping defect detection comprising following steps:

providing a sample, the sample comprising:

a silicon substrate;

a plurality of electric devices disposed on the silicon substrate, the plurality of electric devices comprising a gate;

a dielectric layer covering the plurality of electric devices and the silicon substrate, the dielectric layer having a plurality of contact holes disposed on each of the electric devices, wherein at least a void is formed between two adjacent gates due to low uniformity of the dielectric layer coverage; and a polysilicon layer covering the dielectric layer and electrically connecting to the electric devices through the contact holes, wherein the polysilicon film fills the contact holes to form a plurality of contact plugs and fills the void to form a piping defect;

performing a chemical mechanical polishing (CMP) process to remove the polysilicon layer and over polish the dielectric layer;

performing a wet etching process to etch the dielectric layer selectively; and inspecting the sample with a light source to search for the piping defect, wherein the polysilicon layer appears opaque but the dielectric layer appears transparent under the light source.

2. The method of claim 1 wherein the chemical mechanic polishing process is performed until the contact plugs are not overlapping above the gates.

3. The method of claim 1 wherein the light source comprises ultraviolet (UV) light.

4. The method of claim 3 wherein the ultraviolet light comprises broadband UV light or narrowband UV light.

5. The method of claim 1 wherein each of the electric devices is a MOS transistor, each MOS transistor comprising a gate disposed on the surface of the substrate, and further comprising a source and a drain disposed on both sides of the gate.

6. The method of claim 1 wherein the dielectric layer comprises a borophospho-tetra-ethyl-otho silicate (BPTEOS) layer.

7. The method of claim 1 further comprising performing a defect classification by utilizing an automatic defect classification (ADC) tool.

8. The method of claim 1 further comprising reviewing with a scanning electron microscope (SEM) after finding the location of the piping defect for analyzing the piping defect in advance.

9. A method of defect detection for a semiconductor wafer, the method comprises following steps:

providing a semiconductor wafer comprising:

a silicon substrate; and a dielectric layer positioned on the silicon substrate;

performing a pretreatment process to remove parts of the dielectric layer; and inspecting the semiconductor wafer under ultraviolet light irradiation and judging the existence of the defect in the dielectric layer according to brightness differences in the image of the semiconductor wafer.

10. The method of claim 9 wherein when a piping defect is present in the dielectric layer, a high brightness image is formed in the region of the piping defect under UV light irradiation.

11. The method of claim 9 wherein the defect has a line width less than 0.1 $\mu$m.

12. The method of claim 9 wherein the pretreatment process comprises a chemical mechanic polishing process and a wet etching process.

13. The method of claim 9 wherein the semiconductor wafer further comprises a plurality of electric devices disposed on the surface of the silicon substrate.

14. The method of claim 9 wherein the dielectric layer comprises a borophospho-tetra-ethyl-otho silicate (BPTEOS) layer.

15. The method of claim 9 wherein the ultraviolet light comprises broadband UV light or narrowband UV light.

16. The method of claim 9 further comprising performing a defect classification by utilizing an automatic defect classification (ADC) tool.

17. The method of claim 9 further comprising reviewing with a scanning electron microscope (SEM) after finding the location of the defect for analyzing the found defect in advance.

* * * * *